US007687232B2

(12) United States Patent
Gyllensten et al.

(10) Patent No.: US 7,687,232 B2
(45) Date of Patent: Mar. 30, 2010

(54) METHOD FOR ESTIMATING THE RISK OF CARCINOMA DEVELOPMENT

(75) Inventors: Ulf Gyllensten, Uppsala (SE); Martin Moberg, Uppsala (SE)

(73) Assignee: Cepheid, Sunnyvale, CA (US)

( * ) Notice: Subject to any disclaimer, the term of this patent is extended or adjusted under 35 U.S.C. 154(b) by 645 days.

(21) Appl. No.: 10/529,446

(22) PCT Filed: Oct. 1, 2003

(86) PCT No.: PCT/SE03/01530

§ 371 (c)(1),
(2), (4) Date: Nov. 28, 2005

(87) PCT Pub. No.: WO2004/031417

PCT Pub. Date: Apr. 15, 2004

(65) Prior Publication Data

US 2006/0121482 A1    Jun. 8, 2006

(30) Foreign Application Priority Data

Oct. 1, 2002    (SE)    ................................. 0202896

(51) Int. Cl.
*C12Q 1/68*    (2006.01)
(52) U.S. Cl. .......................................... 435/6; 435/69.1
(58) Field of Classification Search .................... 435/6, 435/69.1
See application file for complete search history.

(56) References Cited

U.S. PATENT DOCUMENTS

| 6,228,368 | B1 | 5/2001 | Gissmann et al. |
| 6,420,106 | B1 | 7/2002 | Gyllensten et al. |
| 2002/0137021 | A1 | 9/2002 | Kroeger et al. |
| 2007/0037137 | A1 | 2/2007 | Gyllensten et al. |

OTHER PUBLICATIONS

Ruth Ann Tucker et al, "Real-time PCR-based Fluorescent Assay for Quantitation of Human Papillomavirus Types 6, 11, 16, and 18", *Molecular Diagnosis*, vol. 6, No. 1, 2001, pp. 39-47.
David C. Swan et al, "A Sensitive, Type-Specific, Fluorogenic Probe Assay for Detection of Human Papillomvarisu DNA", *Journal of Clinical Microbiology*, vol. 35, No. 4, Apr. 1997, pp. 886-891.
Toshiyuki Sasagawa et al, "High-Risk and Multiple Human Papillomavirus Infections Associated with Cervical Abnormalities in Japanese Women", *Cancer Epidemiology, Biomarkers & Prevention*, vol. 10, Jan. 2001, pp. 45-52.
D.Y. Chang et al, "Prevalence of single and multiple infection with human papillomaviruses in various grades of cervical neoplasia", *Journal of Medical Microbiology*, vol. 46, 1997, pp. 54-60.
Susanne K. Kjaer et al, "Type specific persistence of high risk human papillomavirus (HPV) as indicator of high grade cervical squamous intraepithelial lesions in young women: population based prospective follow up study", *BMJ*, vol. 325, Sep. 14, 2002, pp. 1-7.

Steven M. Anderson et al, "Human Papillomavirus and Cervical Cancer", *Clinical Microbiology Newsletter*, vol. 24, No. 15, 2002, pp. 113-118.
Agnetha M. Josefsson et al, "Viral load of human papilloma virus 16 as a determinant for development of cervical carcinoma in situ: a nested case-control study", *The Lancet*, vol. 355, Jun. 24, 2000, pp. 2189-2193.
Agnetha Josefsson et al, "Detection and Quantitation of Human Papillomavirus by Using the Fluorescent 5' Exonuclease Assay", *Journal of Clinical Microbiology*, vol. 37, No. 3, Mar. 1999, pp. 490-496.
Kenneth Livak et al, "Towards fully automated genome-wide polymorphism screening", *Nature Genetics*, vol. 9, Apr. 1995, pp. 341-342.
Attila T. Lorincz et al, "Viral load of human papillomavirus and risk of CIN3 or cervical cancer", *The Lancet*, vol. 360, Jul. 20, 2002, pp. 228-229.
Martin Moberg et al, "Real-Time PCR-Based System for Simultaneous Quantification of Human Papillomavirus Types Associated with High Risk of Cervical Cancer", *Journal of Clinical Microbiology*, vol. 41, No. 7, Jul. 2003, pp. 3221-3228.
David R. Scott et al, "Use of Human Papillomavirus DNA Testing to Compare Equivocal Cervical Cytologic Interpretations in the United States, Scandinavia, and the United Kingdom", *Cancer Cytopathology*, pp. 14-20, 2002 American Cancer Society.
C.A. Sun et al, "Viral load of high-risk human papillomavirus in cervical squamous intraepithelial lesions", *International Journal of Gynecology& Obstetrics*, 76, 2002, pp. 41-47.
Mark van Duin et al, "Human Papillomavirus 16 Load in Normal and Abnormal Cervical Scrapes: An Indicator of CIN II/III and Viral Clearance", *Int. J. Cancer*, 98, 590-595 (2002).
Thomas C. Wright, Jr. MD, et al, "2001 Consensus Guidelines for the Management of Women with Cervical Cytological Abnormalities", *JAMA*, Apr. 24, 2002, vol. 287, No. 16, pp. 2120-2129.
Nathalie Ylitalo et al, "Detection of Genital Human Papillomavirus by Single-Tube Nested PCR and Type-Specific Oligonucleotide Hybridization", *Journal of Clinical Microbiology*, vol. 33, No. 7, Jul. 1995, pp. 1822-1828.

(Continued)

*Primary Examiner*—Ali R. Salimi
(74) *Attorney, Agent, or Firm*—Porter, Wright, Morris & Arthur LLP

(57) ABSTRACT

The present invention relates to a method for estimating the risk for development of carcinoma in an individual. More precisely, for estimating the cancer risk in an individual being exposed to human papilloma virus(es) (HPV). The method comprises (i) identification of one or more of said HPV or groups thereof in a sample from said human being;
(ii) calculating the amount of HPV of each type or group in the sample and normalising the values to the amount of cells sampled;
(iii) estimating the risk for each of the HPV or groups of HPV by comparing each viral titer value from (ii) with type or group specific standard curves for each viral type or group with risk estimation values; and
(iv) estimating the combined risk for carcinoma development for the human being from the individual risk estimation curves of the different viral types.

15 Claims, 4 Drawing Sheets

OTHER PUBLICATIONS

Figure 2A:
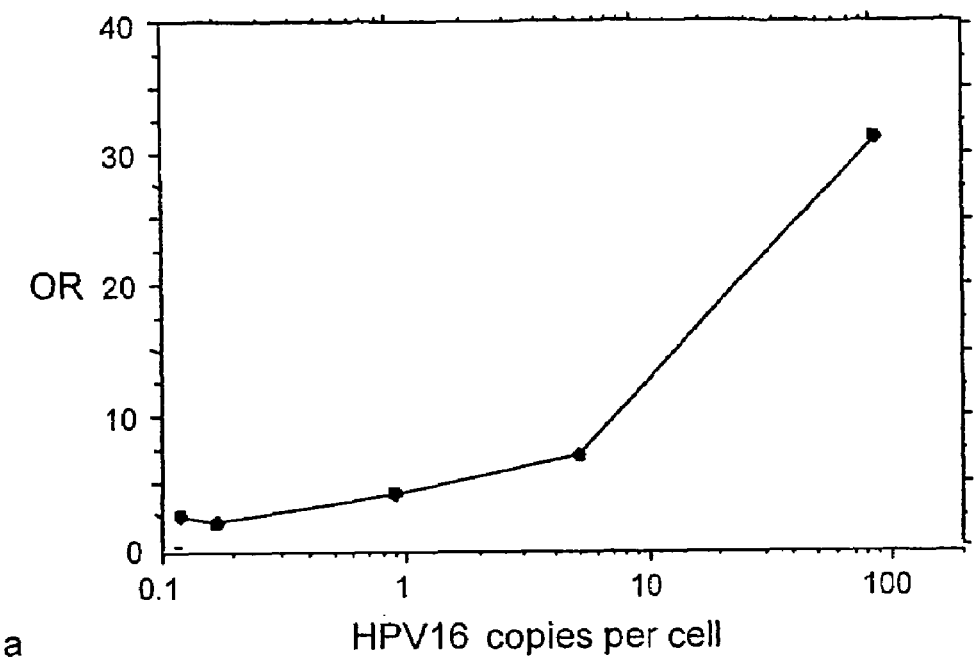

Nathalie Ylitalo et al, "Consistent high viral load of human papillomavirus 16 and risk of cervical carcinoma in situ: a nested case-control study", *The Lancet*, vol. 355, Jun. 24, 2000, pp. 2194-2198.

David C. Swan et al, "Human Papillomavirus (HPV) DNA Copy No. Is Dependent on Grade of Cervical Disease and HPV Type", *Journal of Clinical Microbiology*, Apr. 1999, vol. 37, No. 4, pp. 1030-1034.

Marich et al, Human papillomavirus type 35 complete genome. GenBank Accession No. M74117 (2002).

Marich et al, The phylogenetic relationship and complete nucleotide sequence of human papillomavirus type 35, Virology, 186(2):770-776 (1992).

Yoo et al, Homo sapiens hydroxymethylbilane synthase gene. GenBank Accession No. M95623 (1995).

Yoo et al, Homo sapiens hydroxymethylbilane synthase: complete genomic sequence and amplifiable polymorphisms in the human gene, Genomics, 15:21-29 (1993).

Buck et al, Design strategies and performance of custom DNA sequencing primers, BioTechniques, 27:528-536 (1999).

Goldsborough et al, Nucleotide sequence of human papillomavirus type 31: a cervical neoplasia-associated virus. GenBank Accession No. J04353 (1994).

Seedorf et al, Identification of early proteins of the human papilloma viruses type 16 (HPV 16) and type 18 (HPV 18) in cervical carcinoma cells. EMBO J., 6:139-144 (1987).

Sastre-Garau et al, Distinct patterns of alteration of myc genes associated with integration of human papillomavirus type 16 or type 45 DNA in two genital tumors, J. Gen. Virol., 81:1983-1993 (2000).

Sastre-Garau et al, Distinct patterns of alteration of myc genes associated with integration of human papillomavirus type 16 or type 45 DNA in two genital tumors. GenBank Accession No. AJ242956 (2006).

Fig. 1 a and 1b.
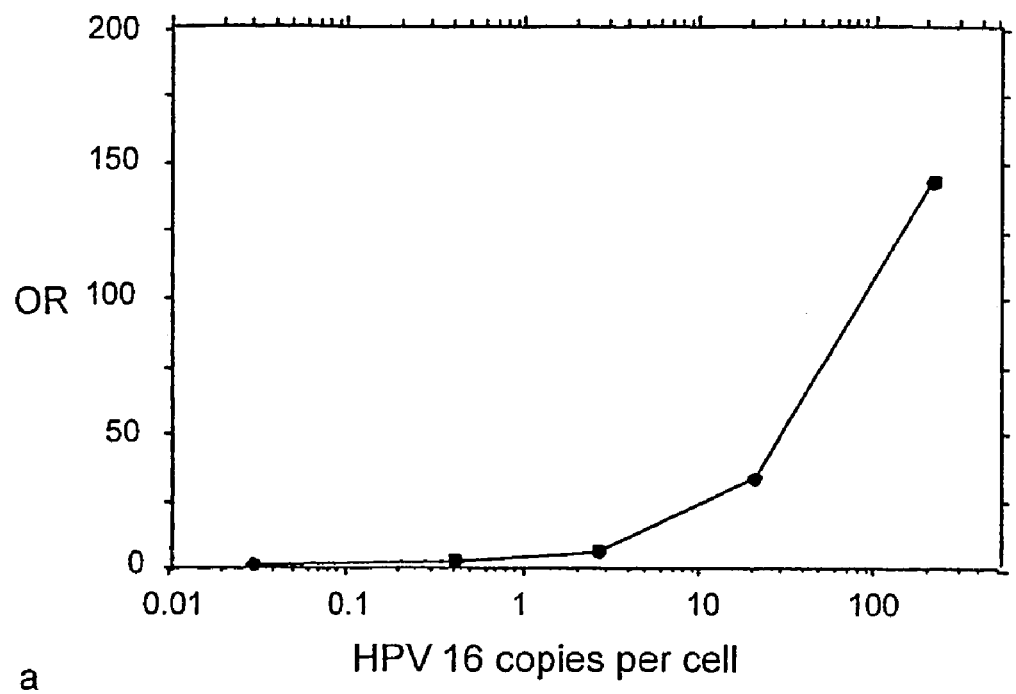
a
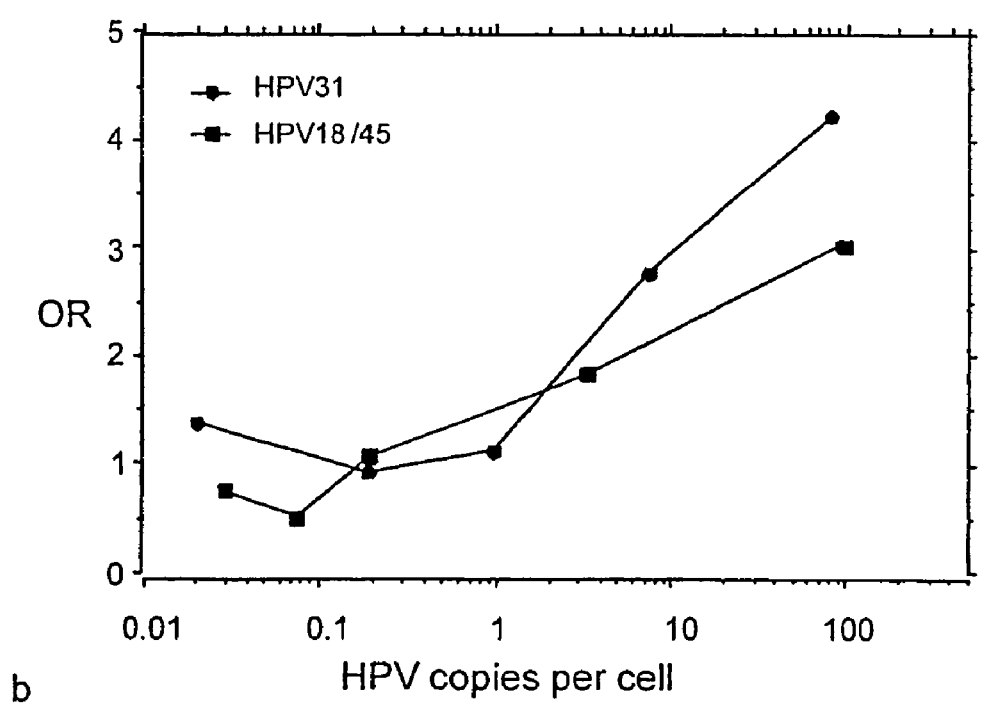
b

Fig. 1 c and 1d.
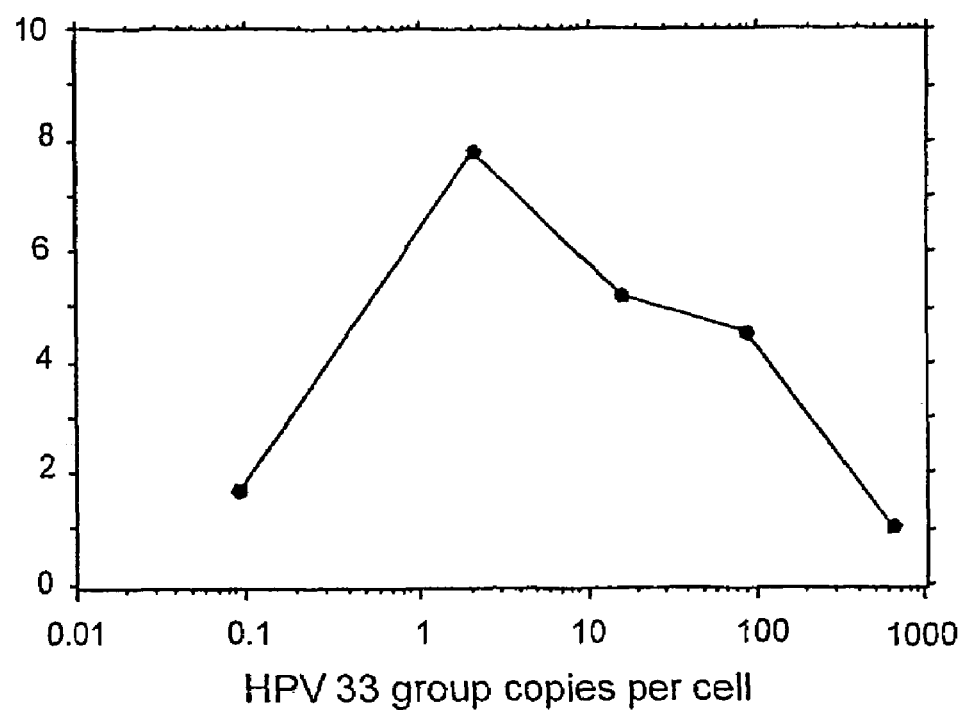
c
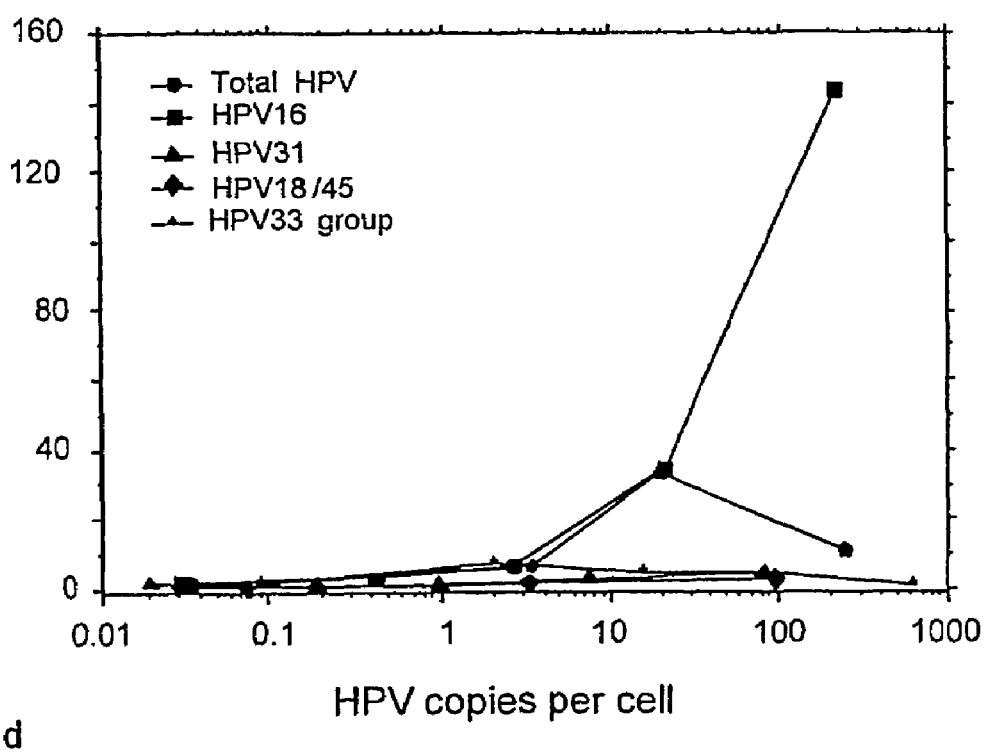
d a b

METHOD FOR ESTIMATING THE RISK OF CARCINOMA DEVELOPMENT

RELATED APPLICATIONS

This application is a 371 of PCT/SE2003/001530.

FIELD OF THE INVENTION

The present invention relates to a method for estimating the risk for development of carcinoma in an individual. More precisely, for estimating the cancer risk in an individual being exposed to human papilloma virus(es) (HPV).

BACKGROUND OF THE INVENTION

Cervical carcinoma is considered to be the third most common cancer in women in the world. Infection by certain types of human papillomavirus (HPV), in particular HPV 16 and HPV 18, increases the risk for cervical cancer. Although HPV infection is common among young women, only less than 1% of those testing positive for oncogenic HPV types at screening develop cervical cancer. There is an increased risk of developing cervical carcinoma in situ (CIS) with increasing amounts of the HPV 16 DNA in cervical smear samples (Josefsson et al. 2000; Ylitalo et al. 2000). HPV load has been studied using different designs, disease outcomes and techniques for viral load determination. van Duin et al. (2002), using a nested case-control design, show that women with high HPV 16 DNA titer in smears normal by cytology have an increased risk of later developing cervical interstitial neoplasia of grade 2 and 3 (CIN2/CIN3). Also, using a case-control study Sun et al. (2002) showed an increased risk of squamous intraepithelial lesions (SIL) with higher amounts of HPV. By contrast, Lorincz et al. (2002) did not find an increased risk of CIN3 or cervical cancer with higher viral titers.

U.S. Pat. No. 6,420,106 describes a method to predict the risk of progression to virus associated cancer in a human subject. This method utilizes virus titer as a basis for the analysis.

SUMMARY OF THE INVENTION

The object of the present invention was to provide a method for estimating the risk for development of carcinoma in an individual. The inventors have studied the relationship between amount of HPV DNA and development of cervical carcinoma in situ (CIS). For this purpose a large material of archival cervical smears collected during routine gynecological health controls, representing cases with CIS and individually matched population controls, was analyzed. This was made using the newly developed assay that permits the viral load of a range of high-risk HPV types to be estimated and normalized by sample amount. The method and kit for performing this assay is described in the copending patent application PCT/SE02/1529.

According to the present invention the amounts of HPV DNA in a series of the most frequent high-risk HPV types are used as determinants of progression to CIS. The viral load of individual high-risk FTP V-types is determined and these values are each compared with their standard curve with risk estimation values. The combined comparisons gives the estimated cancer risk. Thus, several different viral load values are needed to provide the estimated cancer risk. The present invention enables distinction between HPV infections with a high or low risk of progressing into CIS.

In this invention a PCR assay is employed based on the 5'-exonuclease (Taqman) method to estimate the copy number for individual HPV types, or groups of viral types, for ten of the most frequent high-risk HPV types in 495 cases of CIS and 649 matched population controls. Analysis of a single copy nuclear gene is used to derive an estimate of the HPV copy number per genome equivalent in individual samples. In total, 2999 archival smear samples from gynecologic health control, collected over a period of up to 26 years, were analyzed to assess the viral load pattern during infection history. The method may be further optimized by refining the standard curves on the basis of several measurements and the outcome for sampled patients, i.e. if they have developed cancer or not.

The procedure for collection of epithelial cells results in widely different amounts between samples, and case smears generally have higher amount of cells. This underscores the need for normalization of HPV copy number to sample amount. The risk of developing CIS increases with higher normalized viral titer for most HPV types, with exception of the group of viruses HPV 33, 52, 58 and 67. The association between viral titer and risk of cancer is seen both when the analysis is based on the first smear from each woman (collected on average 7.8 years before cancer diagnosis and classified as normal by cytology on squamous cells) and when based on the mean viral load of all HPV positive smears from a woman. The range of copy numbers per cells does not differ between HPV types, but the risk associated with a particular viral load is dramatically higher for HPV 16 than for types such as HPV 31, 18 or 45.

The results show that estimates of the HPV DNA amount can be used to predict risk of CIS at a stage when cytology screening is not informative. HPV titer analysis has to be based on type-specific estimates of copy number to be fully informative and estimates should be normalized for sample amount. Inclusion of a type-specific assay of HPV DNA viral load in the gynecological health control increases the ability to distinguish between infections with a high or low risk of progressing into CIS.

Thus, the present invention provides a method for estimating the risk for development of carcinoma in a human being exposed to human pailloma virus(es) (HPV), comprising the following steps (i) identification of one or more of said HPV or groups thereof in a sample from said human being;

(ii) calculating the amount of HPV of each type or group in the sample and normalising the values to the amount of cells sampled;

(iii) estimating the risk for each of the HPV or groups of HPV by comparing each viral titer value from (ii) with type or group specific standard curves for each viral type or group with risk estimation values; and (iv) estimating the combined risk for carcinoma development for the human being from the individual risk estimation curves of the different viral types.

In step (i) the identification may be of one or several groups of HPV.

Preferably, step ii) is made using the method and kit described in the copending application PCT/SE02/1529.

However other methods for calculating the amount of different HPV types may also be used.

The amount of HPV may be determined by amplification, preferably PCR amplification, more preferably a PCR assay based on the 5'-exonuclease (Taqman) method.

The best results have been achieved with HPV 16, 18, 31, 33, 35, 39, 45, 52, and 58. However, the method according to the present invention can be carried out with a subset of said viruses as well as other HPV and combinations thereof.

The risk estimation values may be odds ratio (OR), relative risk (RR) and/or positive predictive values (PPV) or other measures of relative or absolute risk.

The method of the invention may be used to indicate the risk of cancer in a number of organs, such as cervical, vulvar, vaginal, anal, penile, oropharyngeal and skin cancer.

In one embodiment, the human being is a woman and the carcinoma is cervical carcinoma in situ (CIS).

In this latter case, the age of the woman may be optionally taken into account in steps (iii) and/or (iv).

Methods

Subjects

The study design has been described previously (Josefsson et al. 2000). Briefly, the women included in the case-control study were selected from a cohort comprising women resident in Uppsala County, Sweden, between 1969-1995 (Ylitalo et al. 1999). To identify all eligible cases of CIS, information from the organized screening program between 1969 and 1995 was merged to the National Cancer Registry. Women included in the study had to fulfill the following entry criteria a) born in Sweden, b) less than 50 years of age at entry, c) their first smear classified as normal by cytology on squamous cell (PAP=1). For each case, five separate controls, individually matched by date of entry to the cohort (+/−90 days) and by year of birth, were randomly selected from the study cohort. The women included as controls should also be alive without having developed CIS or invasive cancer before the date of diagnosis for their corresponding matched case. The cases and controls were matched with respect to age and time (calendar) at which the first smear was collected. Similar to the cases, the controls also had the first smear classified as normal by cytology on squamous cell (PAP=1). The study was approved by the local ethics committees.

DNA Extraction

DNA was purified from archival Papanicolaou stained smears using published procedures (Josefsson et al. 1999). The procedure includes xylene incubation, destaining in 99.5% ethanol, proteinase K treatment (60° C., minimum 1 hour) and subsequently protein precipitation in saturated ammonium acetate. The DNA in the supernatant is then recovered with ethanol, the pellet washed with 70% ethanol, dried and dissolved in 200 µl TE-low (10 mM Tris-HCL, pH 7.4, 0.1 mM EDTA).

Quantification Assay

The system for quantification of the 10 HPV types (HPV 16, 18, 31, 33, 35, 39, 45, 52, 58 and 67) has been described (Moberg et al. 2002). The template of the present invention may further comprise HPV 51, 56, 59 and 68. Briefly, the PCR amplification is performed in a 25 µl volume containing 1× Buffer A (Applied Biosystems, Foster City, Calif., USA), 3.5 mM MgCl$_2$, 200 nM each of dATP, dCTP, dGTP and 400 nM dUTP (Pharmacia Biotech, Uppsala, Sweden), 0.625U AmpliTaq Gold (Applied Biosystems, Foster City, Calif., USA), 3.1 µg BSA (Sigma) and 200 nM of each primer and probe, and 3 µl of sample DNA. The primers and probes have been described (Moberg et al. 2002). Each smear sample is measured in three different PCRs: Reaction 1 detects and quantifies HPV types 16, 31, 18 and 45 (HPV 18 and 45 detected and quantified together), Reaction 2 detects and quantifies HPV types 33, 35, 39, 52, 58 and 67 (HPV 33, 52, 58 and 67 detected and quantified together) and Reaction 3 detects and quantifies the amount of a human single copy gene (Moberg et al. 2002). Amplification and detection is performed using a 7700 Sequence Detection System (Applied Biosystems, Inc., Foster City, Calif., USA). The amplification ramp includes an initial hold program of 10 min. at 95° C. to release the activity of the Taq DNA polymerase. The hold step is followed by a two-step cycle consisting of 15 sec. at 95° C. and 1 min. at 57° C., and the two-step cycle is repeated 40 times. Reactions including all PCR components, but without template DNA (denoted NTC reactions), are used to ensure that the reagents mix is free of contamination.

Calculation of Copy Number

The Sequence Detection System software (Applied Biosystems, Foster City, Calif., USA) is used to produce a file with raw data. A computer program has been developed to handle quantification of multiple fluorophores in the same PCR and used for calculation of threshold cycle number and, based on standard curves for each viral type, the HPV copy numbers per cell.

Statistical Analyses

Odds ratios are estimated with 95% confidence intervals and p-values using logistic regression (LOGISTIC procedure in SASv6.12 software).

Results

Cohort Definition

The nested case-control study initially included 504 cases and 662 controls. From some controls there was only one smear available during the follow-up period and a second control was therefore randomly chosen from the original pool of controls to increase the statistical power. After the cytological and histological review the study included 499 cases, 499 first controls and 158 of the second set of controls. Controls that had undergone hysterectomy prior to the diagnosis of their corresponding case were then excluded, leaving 495 cases, 495 first controls and 154 second controls. Due to insufficient amount of sample 16 smears from cases and 9 smears from controls were excluded, as were 232 smears from cases and 223 smears from controls that were negative for the human single copy gene and therefore would not allow for normalization of HPV-DNA copy number by sample amount. The remaining 462 cases of CIS (1516 smears) and 569 controls (1483 smears) had at least one smear positive for human DNA from each women and were included in the study (Table 1). The median number of smears positive for human DNA was 2 for both cases and controls, with a somewhat wider range for the cases (Table 1).

DNA Amount in Samples

The number of copies of the human nuclear gene varies substantially between samples, from a low of 1.1 copies in the sample volume to a high of 17.000, indicating that the sampling procedure and DNA recovery protocol may result in very different amounts of biological material. The median number of human gene copies is higher in the case smears (69.7) than in the controls smears (53.4), showing that more epithelial cells are recovered from women that will develop CIS. The large variation in amount of cells between samples and the higher cell number in cases indicates that normalization for the amount of cells is necessary to obtain comparable results studies or between clinical laboratories.

HPV Amount and Cancer Risk

HPV 16

A total of 806 smears (53%) from cases and 219 smears (15%) from controls type positive for HPV 16 (Table 1). A total of 167 cases have no history of HPV 16 infection as compared to 410 controls. The occurrence of at least two HPV 16 positive smears is more common among cases (184 women) than among the controls (39 women). The median and maximum HPV 16 copy number is higher for cases than for the controls, both using non-normalized and normalized estimates (Table 1). The maximum HPV 16 copy number is substantially lower when normalized for amount of cellular DNA in the sample.

The relationship between amount of HPV 16 DNA and risk of disease (CIS) was studied using conditional logistic regression analysis to estimate odds ratio (OR). In this analysis we removed smears taken later than one year before diagnosis, since among the women developing CIS additional smears were often taken as part of the diagnostic work-up. The mean number of smears per case after this exclusion is similar between cases (2.9) and controls (2.2). In calculating the OR, adjustments were made for the mean calendar period of smear collection (to correct for any temporal trends) and the total number of smears per woman (to minimize the effect of variable number of smears available from different women). Similar adjustments were made in analyzing the data for the other HPV types. The OR based on the mean copy number of all HPV 16 infected smear samples from a woman, not normalized for sample amount, shows a strong increasing trend with higher amount of HPV DNA and reaches over 60 for women in the highest titer percentile (Table 2a). The OR is statistically significant for each titer quintile except the first (fable 2a). The OR for the normalized HPV 16 copy number per cell shows an even more marked increase and reaches over 140 for the highest percentile. The OR is statistically significant for all the percentiles.

To study the relationship between HPV titer and risk of CIS development at a stage when cytology on squamous cells did not provide any information, the analysis was based on the first smear collected from each woman. These smears were normal by cytology on squamous cells and collected on average 7.8 years before diagnosis. The OR for the first smear from each woman shows a strong increasing trend with higher amount of HPV 16 DNA and reaches above 30 in the highest quintile for the normalized data (Table 3a). The OR in the analysis of normalized data is significant for all quintiles (Table 3a). Only one smear per woman is included in this analysis and the relationship between viral titer and risk of cancer cannot be due to dependence among smears. Also, the controls are matched individually to their case with respect to time of first smear and the results cannot be caused by asymmetric sampling of cases and controls. In the analysis of the first smear we initially adjusted for the women's age at sample collection, the time span between the sampling and CIS diagnosis and the calendar period of smear collection. None of these adjustments affected the OR and the values presented are therefore for the unadjusted analysis. The same adjustments were made in the calculations for the other HPV types discussed below.

HPV 31

A total of 209 smears (14%) from cases and 112 smears (7.5%) from controls typed positive for HPV 31 (Table 1). A total of 366 cases have no history of HPV 31 infection as compared to 486 controls. The presence of multiple (at least two) smears with HPV 31 is more common among cases (42 women) relative to the controls (19 women). The median and maximum HPV 31 copy number per sample is higher for cases than for the controls, as is the normalized HPV 31 copy numbers per cell (Table 1). The OR based on the mean copy number of all HPV 31 positive smears from a woman is statistically significant for the two highest quintiles, both for normalized and non-normalized data and the OR for the highest quintiles is about 4 (Table 2b). The OR for the first smear increases with higher amount of HPV 31 DNA and is significant for the two highest quintiles using normalized data (Table 3b).

HPV 18/45

The typing system combines HPV 18 and HPV 45 into one group. A total of 257 smears (17%) from cases and 196 smears (13%) from controls are positive for HPV 18/45 (Table 1). 321 cases have no history of HPV 18/45 infection, as compared to 430 controls. The presence of multiple (at least two) smears with HPV 18/45 is also more common among cases (56 women) than among the controls (33 women). The median and maximum HPV 18/45 copy number is higher for cases than for the controls (Table 1). The difference is most pronounced for non-normalized data, but for the normalized data the maximum difference between cases and controls is still about 10-fold. The OR based on the mean copy number of HPV 18/45 positive smears from a woman is increases with higher copy number and is statistically significant for the highest quintile, both for normalized and non-normalized data (Table 2c). The OR for the first smear also increases with higher amount of HPV 18/45 DNA and is significant for the highest quintile in the analysis, both for the normalized and non-normalized data (Table 3c).

HPV 33 Group

According to one embodiment of the invention the typing system combines HPV 33, 52, 58 and 67 into one group. A total of 191 smears (12.6%) from cases and 64 smears (4.3%) from controls are positive for the HPV 33 group (Table 1). A total of 360 cases have no history of HPV 33 group infection as compared to 521 controls. The presence of multiple smears infected with viruses from the HPV 33 group is more common among cases (40 women) relative to the controls (14 women). In contrast to the pattern for the other HPV types both the median and maximum copy number per sample for the HPV 33 group is higher for controls than for cases (Table 1). However, the normalized copy number per cell is slightly higher for the cases. The OR for the mean copy number of all HPV 33 group positive smears from a woman is statistically significant for all quintiles, both for the normalized and non-normalized data (Table 2d). However, the OR for the HPV 33 group peaks at the middle titer quintile rather than at the highest quintile. This pattern is seen both for the non-normalized (peak OR=15.2) and normalized data (OR=5.2). The OR for the first smear positive for human DNA shows a similar trend, although the data is not significant for any of the quintiles (Table 3d). According to an at present preferred embodiment of the invention HPV 67 is eliminated from this group.

Other HPV Types

Other HPV types (HPV 35, n=27, and HPV 39, n=20) occur at a frequency that is too low to examine the relationship between titer and risk of CIS.

TABLE 1 cont. Baseline data for the study

| | Cases | Controls |
| --- | --- | --- |
| HPV 18/45-positive smears | | |
| Total | 257 | 196 |
| No positive smears | 321 | 430 |
| ≧2 positive smears | 56 | 33 |
| HPV 18/45 Copies/sample | | |
| Median | 70.5 | 9.6 |
| Maximum | 7402311 | 235369 |

TABLE 1-continued cont. Baseline data for the study

|  | Cases | Controls |
|---|---|---|
| Copies/cell |  |  |
| Median | 1.6 | 0.3 |
| Maximum | 17396.9 | 1853.9 |
| HPV 33-group-positive smears |  |  |
| Total | 191 | 64 |
| No positive smears | 360 | 521 |
| $\geq$ 2 positive smears | 40 | 14 |
| HPV 33-group copies/sample |  |  |
| Median | 844.7 | 1015.9 |
| Maximum | 223331 | 319316 |
| HPV 33-group copies/cell |  |  |
| Median | 13.5 | 19.6 |
| Maximum | 21767.1 | 18537.3 |

TABLE 2

Odds ratios for different viral types.

| Quintiles | Cases/Controls | Odds Ratio | 95% C.I. Limits | |
|---|---|---|---|---|
|  |  |  | Low | High |
| a) HPV 16 mean value | | | | |
| Copies | | | | |
| n < 1 | 167/410 | Referent | — | — |
| 1 <= n < 5.1 | 26/65 | 1.3 | 0.6 | 2.4 |
| 5.1 <= n < 21.4 | 38/56 | 2.3 | 1.2 | 4.5 |
| 21.4 <= n < 177.9 | 67/23 | 9.4 | 4.8 | 18.7 |
| 177.9 <= n < 1321.8 | 77/10 | 24.1 | 10.4 | 55.9 |
| 1321.8 <= n | 87/5 | 62.5 | 21.5 | 181.5 |
| Copies/cell | | | | |
| n < 0 | 167/410 | Referent | — | — |
| 0 <= n < 0.2 | 31/59 | 2.1 | 1.2 | 3.4 |
| 0.2 <= n < 0.9 | 42/50 | 3.5 | 1.9 | 6.5 |
| 0.9 <= n < 6.2 | 54/37 | 6.7 | 3.4 | 13.0 |
| 6.2 <= n < 61.2 | 81/10 | 34.3 | 14.8 | 79.6 |
| 61.2 <= n | 87/3 | 143.6 | 39.6 | 520.6 |
| b) HPV 31 mean value | | | | |
| Copies | | | | |
| n < 1 | 366/486 | Referent | — | — |
| 1 <= n < 4.7 | 14/21 | 0.8 | 0.3 | 2.0 |
| 4.7 <= n < 9.9 | 16/23 | 0.9 | 0.3 | 2.6 |
| 9.9 <= n < 37.6 | 14/20 | 1.0 | 0.4 | 2.5 |
| 37.6 <= n < 849.0 | 27/9 | 4.0 | 1.5 | 10.7 |
| 849.0 <= n | 25/10 | 3.4 | 1.2 | 9.7 |
| Copies/cell | | | | |
| n < 0 | 366/486 | Referent | — | — |
| 0 <= n < 0.1 | 17/18 | 1.4 | 0.6 | 3.2 |
| 0.1 <= n < 0.4 | 14/23 | 0.9 | 0.4 | 2.4 |
| 0.4 <= n < 2.6 | 15/20 | 1.1 | 0.5 | 2.8 |
| 2.6 <= n < 23.5 | 24/13 | 2.8 | 1.1 | 7.4 |
| 23.5 <= n | 26/9 | 4.2 | 1.5 | 12.2 |
| c) HPV 18/45 mean value | | | | |
| Copies | | | | |
| n < 1 | 321/430 | Referent | — | — |
| 1 <= n < 4.4 | 20/42 | 0.5 | 0.3 | 1.1 |
| 4.4 <= n < 9.9 | 19/33 | 0.6 | 0.3 | 1.3 |
| 9.9 <= n < 30.3 | 26/28 | 1.1 | 0.5 | 2.4 |
| 30.3 <= n < 353.0 | 33/23 | 1.6 | 0.7 | 3.5 |
| 353.0 <= n | 43/13 | 4.2 | 1.9 | 9.4 |

TABLE 2-continued

Odds ratios for different viral types.

| Quintiles | Cases/Controls | Odds Ratio | 95% C.I. Limits | |
|---|---|---|---|---|
|  |  |  | Low | High |
| Copies/cell | | | | |
| n < 0 | 321/430 | Referent | — | — |
| 0 <= n < 0.07 | 21/35 | 0.8 | 0.4 | 1.6 |
| 0.07 <= n < 0.4 | 18/38 | 0.5 | 0.2 | 1.2 |
| 0.4 <= n < 1.7 | 27/29 | 1.1 | 0.5 | 2.2 |
| 1.7 <= n < 8.0 | 35/21 | 1.8 | 0.8 | 4.0 |
| 8.0 <= n | 40/16 | 3.0 | 1.4 | 6.7 |
| d) HPV 33 group mean value | | | | |
| Copies | | | | |
| n < 1 | 360/521 | referent | — | — |
| 1 <= n < 36.3 | 16/15 | 1.5 | 0.5 | 4.4 |
| 36.3 <= n < 494.0 | 22/7 | 5.0 | 1.6 | 15.4 |
| 494.0 <= n < 1368.8 | 27/3 | 15.2 | 3.5 | 65.6 |
| 1368.9 <= n < 5823.4 | 23/8 | 4.6 | 1.4 | 15.2 |
| 5823.4 <= n | 14/15 | 1.4 | 0.5 | 4.0 |
| Copies/cell | | | | |
| n < 0 | 360/521 | referent | — | — |
| 0 <= n < 0.5 | 17/13 | 1.7 | 0.6 | 4.9 |
| 0.5 <= n < 5.3 | 25/5 | 7.8 | 2.3 | 26.9 |
| 5.3 <= n < 26.7 | 23/7 | 5.2 | 1.6 | 16.9 |
| 26.7 <= n < 229.0 | 23/7 | 4.6 | 1.5 | 14.1 |
| 229.0 <= n | 14/16 | 1.1 | 0.4 | 3.1 |

TABLE 3

Odds ratios for different viral types.

| Quintiles | Cases/Controls | Odds Ratio | 95% C.I. Limits | |
|---|---|---|---|---|
|  |  |  | Low | High |
| a) HPV 16 first smear | | | | |
| Copies | | | | |
| x < 1 | 248/456 | — | — | — |
| 1 <= x < 4.8 | 27/27 | 1.8 | 1.0 | 3.2 |
| 4.8 <= x < 21.4 | 25/29 | 1.6 | 0.9 | 2.8 |
| 21.4 <= x < 177.9 | 44/12 | 6.7 | 3.5 | 13.0 |
| 177.9 <= x < 1383.4 | 49/4 | 22.5 | 8.0 | 63.1 |
| 1383.4 <= x | 48/4 | 22.1 | 7.9 | 61.9 |
| Copies/cell | | | | |
| x < 0 | 248/456 | — | — | — |
| 0 <= x < 0.1 | 35/18 | 3.6 | 1.9 | 6.4 |
| 0.1 <= x < 0.4 | 27/27 | 1.8 | 1.0 | 3.2 |
| 0.4 <= x < 2.1 | 38/17 | 4.1 | 2.3 | 7.4 |
| 2.1 <= x < 17.8 | 42/11 | 7.0 | 3.5 | 13.9 |
| 17.8 <= x | 51/3 | 31.3 | 9.7 | 101.2 |
| b) HPV 31 first smear | | | | |
| Copies | | | | |
| x < 1 | 386/483 | — | — | — |
| 1 <= x < 6.3 | 6/16 | 0.5 | 0.2 | 1.2 |
| 6.3 <= x < 17.5 | 8/12 | 0.8 | 0.3 | 2.1 |
| 17.5 <= x < 143.1 | 10/11 | 1.1 | 0.5 | 2.7 |
| 143.1 <= x < 2384.5 | 14/7 | 2.5 | 1.0 | 6.3 |
| 2384.5 <= x | 17/3 | 7.1 | 2.1 | 24.4 |
| Copies/cell | | | | |
| x < 0 | 386/483 | — | — | — |
| 0 <= x < 0.04 | 8/12 | 0.8 | 0.3 | 2.1 |
| 0.04 <= x < 0.5 | 8/13 | 0.8 | 0.3 | 1.9 |
| 0.5 <= x < 2.6 | 9/12 | 0.9 | 0.4 | 2.3 |

TABLE 3-continued

Odds ratios for different viral types.

| Quintiles | Cases/Controls | Odds Ratio | 95% C.I. Limits Low | High |
|---|---|---|---|---|
| $2.6 \le x < 24.0$ | 15/6 | 3.1 | 1.2 | 8.1 |
| $24.0 \le x$ | 15/6 | 3.1 | 1.2 | 8.1 |
| c) HPV 18/45 first smear | | | | |
| Copies | | | | |
| $x < 1$ | 373/450 | — | — | — |
| $1 \le x < 3.1$ | 8/23 | 0.4 | 0.2 | 0.9 |
| $3.1 \le x < 12.6$ | 11/18 | 0.8 | 0.3 | 1.6 |
| $12.6 \le x < 53.8$ | 10/21 | 0.5 | 0.3 | 1.2 |
| $53.8 \le x < 859.9$ | 16/13 | 1.5 | 0.7 | 3.1 |
| $859.9 \le x$ | 23/7 | 4.0 | 1.7 | 9.3 |
| Copies/cell | | | | |
| $x < 0$ | 373/450 | — | — | — |
| $0 \le x < 0.039$ | 11/19 | 0.7 | 0.3 | 1.5 |
| $0.039 \le x < 0.25$ | 11/19 | 0.7 | 0.3 | 1.5 |
| $0.25 \le x < 1.11$ | 12/18 | 0.8 | 0.4 | 1.7 |
| $1.11 \le x < 7.86$ | 13/17 | 0.9 | 0.4 | 1.9 |
| $7.86 \le x$ | 21/9 | 2.8 | 1.3 | 6.2 |
| d) HPV 33 group first smear | | | | |
| Copies | | | | |
| $x < 1$ | 416/510 | — | — | — |
| $1 \le x < 27.3$ | 4/6 | 0.8 | 0.2 | 2.9 |
| $27.3 \le x < 333.4$ | 6/4 | 1.8 | 0.5 | 6.6 |
| $333.4 \le x < 1496.7$ | 7/3 | 2.9 | 0.7 | 11.2 |
| $1496.7 \le x < 8943.4$ | 4/5 | 1.0 | 0.3 | 3.7 |
| $8943.4 \le x$ | 5/4 | 1.5 | 0.4 | 5.7 |
| Copies/cell | | | | |
| $x < 0$ | 415/510 | — | — | — |
| $0 \le x < 0.2$ | 7/3 | 2.9 | 0.7 | 11.2 |
| $0.2 \le x < 0.3$ | 5/5 | 1.2 | 0.3 | 4.3 |
| $0.3 \le x < 24.2$ | 5/3 | 2.0 | 0.5 | 8.6 |
| $24.2 \le x < 295.9$ | 6/4 | 1.8 | 0.5 | 6.6 |
| $295.9 \le x$ | 3/7 | 0.5 | 0.1 | 2.0 |

Relationship Between OR and Copy Number

This relationship will be described below in association with the accompanying drawings.

FIG. 1. Relationships between the median HPV titer in each quintile and odds ratio (OR). The analyses are based on the mean titer for all smears from a woman infected with the particular virus, a) relationship for HPV 16, b) relationship for HPV 31 and HPV 18/45, c) relationship for the HPV 33 group and d) relationships for HPV 16, HPV 31, HPV18/45, HPV 33 group and for total HPV copy number (irrespective of HPV type).

FIG. 2. Relationships between the median HPV titer in each quintile and odds ratio (OR). The analyses are based on the first smears from each woman, a) relationship for BPV 16, b) relationship for HPV 31 and HPV 18/45, c) relationship for the HPV 33 group and d) relationships for HPV 16, HPV 31, HPV18/45, HPV 33 group and for total HPV copy number (irrespective of HPV type).

Figure 2B:
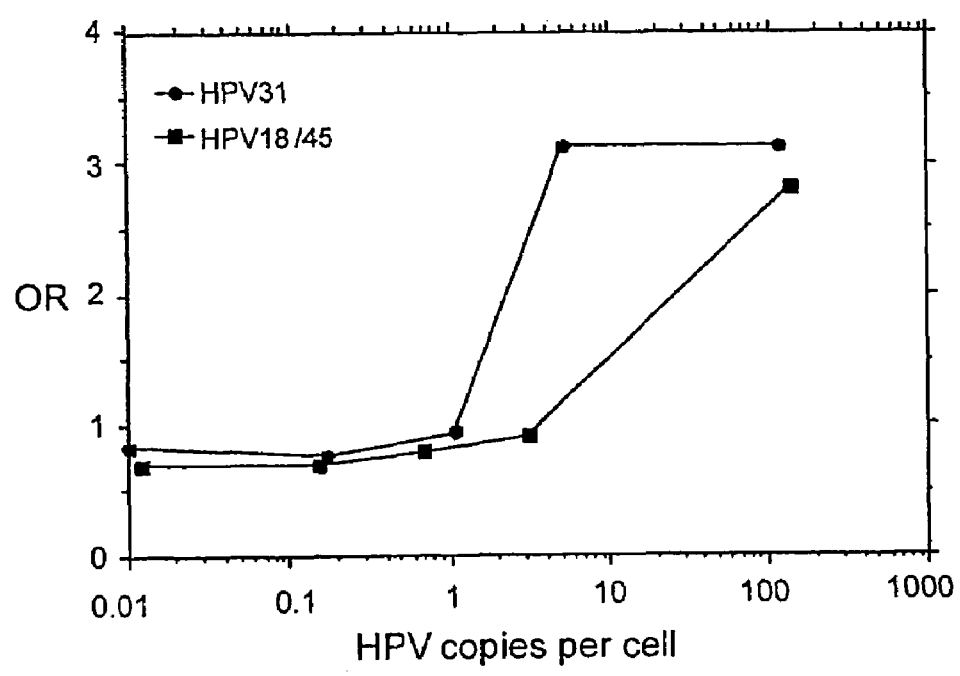
Figure 2C:
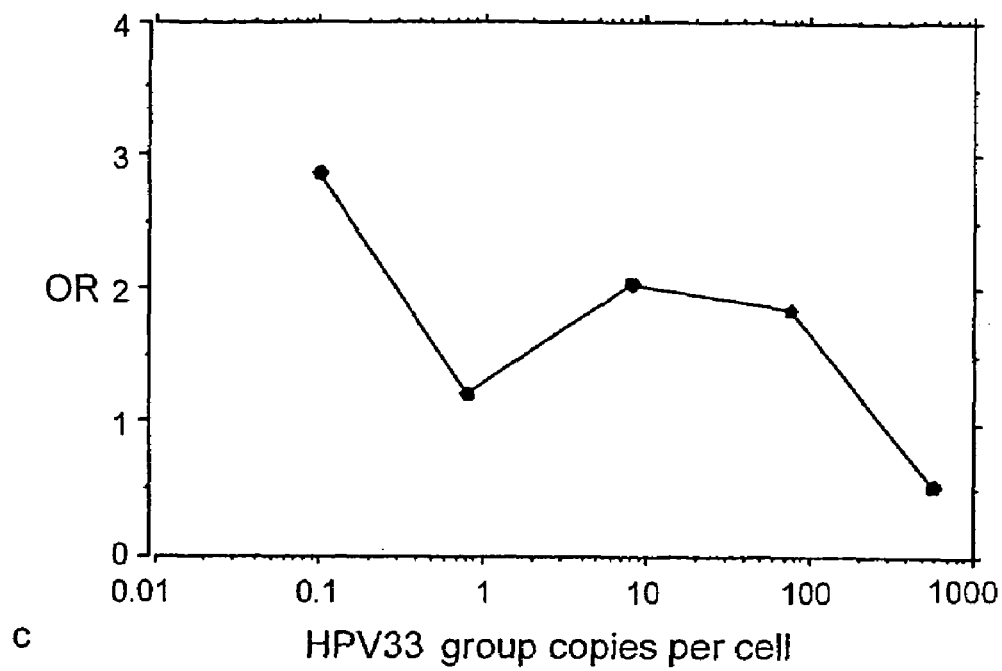
Figure 2D:
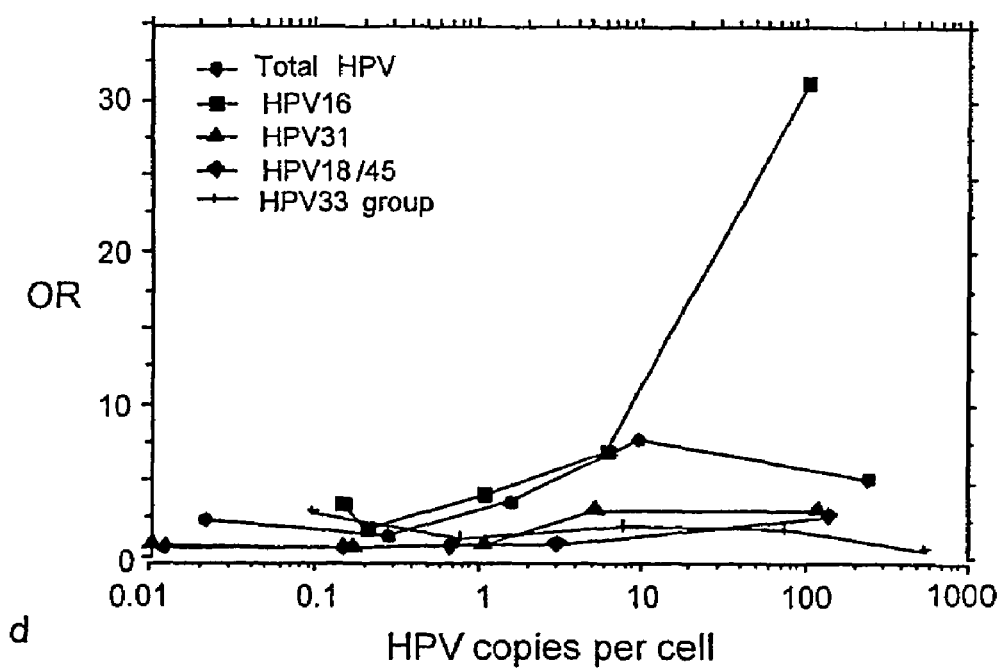

To examine the relationship between viral load and HPV copy number the median HPV copy number for the percentiles was plotted versus OR of CIS. For HPV 16 the OR rises dramatically at copy numbers above 5 copies per cell and reaches a maximum of about 140 (FIG. 1a). A similar rise at about 5 copies per cell is seen when studying the first smear although the OR peaks at 30 at copies per cell (FIG. 2a). For HPV 31 and HPV 18/45 similar positive trends are seen with a final OR of about 3-4 (FIG. 1b, 2b). For these viruses the OR curves are more monotonous. The relationship for the HPV 33 group, including HPV 67, is different and the highest OR is found at an intermediate titer level (FIG. 1c, 2c). The difference in shape and final OR between HPV types is evident when the curves are combined in the same graph (FIG. 1d, 2d). The difference in OR between HPV types cannot be due simply to the copy number since the range in copy numbers is similar for the different viral types. Only the HPV 33 group appears to have a somewhat higher maximum titer. According to an at present preferred embodiment of the invention HPV 67 is eliminated from the HPV 33 group.

The difference in OR curves between HPV types indicate that a typing system that is not able to distinguish between individual HPV types may not accurately estimate the risk for a woman. To the assess the effect on OR of using such a typing system the total number of HPV copies for the types studied in each sample was added up and computed the OR. Using the total number of HPV copies results in a dramatic underestimate of the risk of CIS relative to using the type-specific risk curves (FIG. 2d, 3d). For example, based on the first smear a woman in the highest titer percentile would have an OR of 4 using total HPV copy number while the actual OR is 30. Similarly, using the mean titer a woman in the highest titer interval has an OR of 8 using total HPV copy number and an OR of 140 when based on the type-specific risk curves.

Discussion

The present inventors examine the relationship between viral load and risk of developing cervical carcinoma in situ (CIS) for a series of high-risk HPV types. The risk of CIS increases dramatically with higher amounts of HPV 16 per cell, both for samples taken at a time when the cervical smears have normal cytology and when based on the mean titer value for a woman. This is consistent with previous work, using a different typing system (Josefsson et al. 2000) (van Duin et al. 2002). Other high-risk HPV types also show a significant positive relationship between viral load and risk of CIS. The OR is lower for the non-HPV16 high-risk types although the copy number range is similar between HPV types. Only the HPV 33 group of viruses, which in the example included HPV 67, has a different relationship between viral load and risk of CIS. The deviating pattern for this group may be due to that they are detected together in the typing system or reflect some aspect of their biology. For instance, these viruses may integrate into the host genome more effectively than other HPV types, thereby reducing the number of episomal HPV copies closer to diagnosis. In general, the HPV types studied have markedly type-specific relationships between titer and risk of CIS. Since these differences cannot be explained by differences in viral copy number they must reflect properties of the individual viral types. In particular, HPV 16 is not only the most prevalent high-risk type but also have a very high OR at higher titers.

In the light of type-specific associations between viral load and risk of CIS, a detection method that only provides a summary estimate of the viral amount may not be appropriate for estimating the risk for individual women. For instance, Lorincz et al. (2002) did not find a significant relationship between HPV load and CIS or cervical cancer. These authors argue that differences in the classification criteria between Scandinavian and American pathologists may have resulted in that smears were regarded as normal by the Scandinavian reader but would have been classified as having a typical squamous cells of undetermined significance (ASC-US) or as low-grade squamous intraepithelial lesions (LSIL) by a US reader (Scott et al. 2002). A systematic difference like this may result in different abilities to estimate the risk of cancer from normal smears, depending on the study base. However, an increased risk of CIS for woman with higher viral load is seen both using the first smear and the mean titer for a woman, as well as by others (van Duin et al. 2002). The relationship between HPV titer and risk of cancer is therefore likely to be real. Lorincz et al (2002) may have been unable to detect a relationship as the method they used cannot distinguish between viral types in a sample. The Hybrid Capture II method used measures the combined signal for a number of high-risk HPV types and does not allow for normalization to sample amount. As shown by the present inventors estimating the total HPV copy number may result in a substantial underestimation of the risk for an individual woman.

How can HPV viral titer estimates be used in the clinical screening of pre-stages for cervical cancer? In organized or voluntary cytology screening, where PAP test or liquid cytology is employed as the primary diagnostic tool, qualitative HPV typing has been recommended for specific outcomes. According to the US recommendations, refractory qualitative HPV typing is regarded useful for ASC-US smears and potentially useful for LSIL smears' (Wright et al. 2002). An extension of the HPV typing to include a type-specific titer estimate could be employed to classify samples into three categories; i) uninfected, ii) infected but with a copy numbers in the low-risk interval for the HPV types in the sample, and iii) infected but with a copy number in the high-risk interval for the HPV types in the sample, each category with a specific decision algorithm. A refractory HPV viral titer assay in the screening programs would reduce the screening volume for specific groups, such as those with ASC-US smears or women attending later screening occasions (e.g. at 55 years of age). Also, refractory testing may be employed on smears with normal cytology to identify infections in the high-risk category before they have developed into visible cytology. For example, van Duin et al. (2002) discuss the use of a HPV titer assay as an adjunct to cytology in primary screening of cervical cancer, in particular as an indicator of progression or for management of women with borderline or mild dyskaryosis (MBD). On the basis of their results, van Duin et al. (2002) recommends that women with high HPV 16 viral titer (4.3× $10^6$ copies per sample) be referred directly for colposcopy-directed biopsy since they are at risk of developing high grade SIL.

Given the paramount role of HPV in cervical cancer etiology the potential exist for including a HPV titer assay also in primary screening. According to such a scenario, women testing negative would be referred to the regular screening program, women with titer in the low-risk interval would be retested within a short time (e.g. 12 months) and women with a titer in the high-risk interval would be retested shortly (e.g. within 1 month) and upon confirmation of their high viral load, referred for colposcopy and histology. Evidently, different scenarios can be visualized for the use of HPV viral load test in the clinical screening. Given the increasing evidence that high viral load precedes the development of visible cytology, the present invention contributes to the creation of efficient screening programs and with the aim to reduce the incidence of cervical cancer.

REFERENCES

Josefsson, A. J., P. K. E. Magnusson, N. Ylitalo, P. Sörensen, P. Qwarforth-Tubbin, P. K. Andersen, M. Melbye, H. O. Adami and U. B. Gyllensten 2000. HPV viral load as a determinant for development of cancer in situ. Lancet 355: 2189-93.

Josefsson, A., K. Livak, and U. Gyllensten. 1999. Detection and real time quantitation of human papillomavirus (HPV) using the fluorescent 5-exonuclease assay (TAQMAN). Journal of Clinical Microbiology, 37, 490-496.

Livak, K. J., J. Marmaro, and J. A. Todd. 1995. Towards fully automated genome-wide polymorphism screening. Nature Genet. 9(4):341-42.

Lorincz, A. T., Castle, P. E., Sherman, M. E., Scott, D. R., Glass, A. G., Wacholder, S., Rush, B. B., Gravitt, P. E., Schussler, J. E., Schiffman, M. 2002. Viral load of human papillomvirus and risk of CIN3 or cervical cancer. Lancet 360: 228-229.

Moberg, M., Gustavsson, I., and Gyllensten, U. A novel system for simultaneous quantification of high risk human papillomavirus types baseb on real-time PCR. Submitted.

Scott, D. R., Hagmar, B., Maddox P., et al. 2002. Use of papillomavirus DNA testing to campare the equivocal cytologic interpretations in the United States, Scandinavia and United Kingdom. Cancer Cytopathology, 96:14-20.

Sun, C. A. Liu, J. F., Wu, D. M., Nieh, S., Yu, C. P., and Chu, T. Y. 2002. Viral load of high-risk human papillomavirus in cervical squamous intraepithelial lesions. International Journal of Gynecology and Obstetrics 76; 41-47.

van Duin M., P. J. F. Snijders, H. F. J. Schrijnemakers, F. J. Voorhorst, L. Rozendaal M. A. E. Nobbenhuis, A. J. C. Vandenbrule, R. H. M. Verheijen, T. J. Helmerhorst, and C. J. L. M. Meijers. 2002. Human pappliomavirus 16 loads in normal and abnormal cervical scrapes: an indicator of CINII/CINIII and viral clearance. Int. J. Cancer: 98,590-595.

Wright, T. C., Cox, J. T., Massaud, L. S., Twiggs, L. B., and Wilkinsson, E. J. 2001 Consensus guidelines for the management of women with cervical cytological abnormalities. JAMA, 287; 2120-2129.

Ylitalo N, Bergstrom T, Gyllensten U. Detection of genital human papillomavirus by single-tube nested PCR and type-specific oligonucleotide hybridization. *J Clin Microbiol* 1995;33:1822-8.

Ylitalo, N., A. Josefsson, P. Sörensen, P. Magnusson, P. K. Andersen, J. Pontén, H. O. Adami, U. Gyllensten, and M. Melbye. 2000. Consistent high viral load of human papillomavirus type 16 and risk for cervical carcinoma in situ. Lancet 355:2194-8.

The invention claimed is:

1. A method for estimating the risk for development of carcinoma in a human being exposed to human papilloma virus(es) (HPV), comprising
    (i) determining normalized amounts of two or more HPV groups and/or types in a sample from said human being using quantitative nucleic acid amplification of said HPV groups and/or types, wherein said determining comprises normalizing results of the quantitative nucleic acid amplification for the amount of cells sampled; and
    (ii) estimating a combined risk for carcinoma development for said human being from individual risk estimation curves of the respective two or more HPV groups and/or types, wherein each individual risk estimation curve is a function of the respective normalized amount.

2. A method according to claim 1, wherein the quantitative nucleic acid amplification is PCR amplification.

3. A method according to claim 1, wherein the two or more HPV groups and/or types are selected from the group consisting of HPV 16, 18, 31, 33, 35, 39, 45, 51, 52, 56, 58, 59, 67 and 68, and combinations thereof.

4. A method according to claim 1, wherein the two or more HPV groups and/or types are selected from the group consisting of HPV 16, 18, 31, 33, 35, 39, 45, 52 and 58, and combinations thereof.

5. A method according to claim 1, wherein the individual risk estimation curves provide odds ratio (OR), relative risk (RR) and/or positive predictive values (PPV).

6. A method according to claim 1, wherein the human being is a woman and the carcinoma is cervical carcinoma in situ (CIS).

7. A method according to claim 2, wherein the two or more HPV groups and/or types are selected from the group consisting of HPV 16, 18, 31, 33, 35, 39, 45, 51, 52, 56, 58, 59, 67 and 68, and combinations thereof.

8. A method according to claim 2, wherein the two or more HPV groups and/or types are selected from the group consisting of HPV 16, 18, 31, 33, 35, 39, 45, 52 and 58, and combinations thereof.

9. A method according to claim 2, wherein the individual risk estimation curves provide odds ratio (OR), relative risk (RR) and/or positive predictive values (PPV).

10. A method according to claim 3, wherein the individual risk estimation curves provide odds ratio (OR), relative risk (RR) and/or positive predictive values (PPV).

11. A method according to claim 4, wherein the individual risk estimation curves provide odds ratio (OR), relative risk (RR) and/or positive predictive values (PPV).

12. A method according to claim 2, wherein the human being is a woman and the carcinoma is cervical carcinoma in situ (CIS).

13. A method according to claim 3, wherein the human being is a woman and the carcinoma is cervical carcinoma in situ (CIS).

14. A method according to claim 4, wherein the human being is a woman and the carcinoma is cervical carcinoma in situ (CIS).

15. A method according to claim 5, wherein the human being is a woman and the carcinoma is cervical carcinoma in situ (CIS).

* * * * *